United States Patent [19]

Herbranson et al.

[11] Patent Number: 4,925,860

[45] Date of Patent: May 15, 1990

[54] STABLE PHARMACEUTICAL COMPOSITION OF 3-(HYDROXYMETHYL)-5,5-DIPHENYL-HYDANTOIN DISODIUM PHOSPHATE ESTER

[75] Inventors: Dale E. Herbranson, Lindenhurst; Earl R. Speicher, Buffalo Grove, both of Ill.; Leonard S. Rosenberg, Flemington, N.J.

[73] Assignee: E. I. Du Pont de Nemours and Company, Wilmington, Del.

[21] Appl. No.: 356,948

[22] Filed: May 25, 1989

Related U.S. Application Data

[63] Continuation-in-part of Ser. No. 82,841, Aug. 5, 1987.

[51] Int. Cl.$^5$ .......................................... A61K 31/135
[52] U.S. Cl. .................................... 514/359; 514/358
[58] Field of Search ................... 514/385, 359, 393; 548/112, 312

[56] References Cited

U.S. PATENT DOCUMENTS 4,260,769  4/1981  Stella ................................... 548/112

OTHER PUBLICATIONS

Varia et al., "Phenytoin Prodrug IV: Hydrolysis of Various 3-(Hydroxymethyl)Phenytoin Esters", Journal of Pharmaceutical Sciences, vol. 73, No. 8, Aug. 1984, (pp. 1068-1090).

Primary Examiner—William R. Dixon, Jr.
Assistant Examiner—J. M. Hunter, Jr.

[57] ABSTRACT

Described is a stable pharmaceutical composition of 3-(hydroxymethyl-5,5-diphenylhydantoin disodium phosphate ester, the prodrug of 5,5-diphenylhydantoin (phenytoin) a commonly used drug for the treatment and management of epilepsy and other types of convulsive states. It has been found that degradation of the prodrug to phenytoin can be controlled by controlling the pH of the composition. Controlling the pH to between 8.3 to 9.4 results in the production of diphenylglycinamide as the primary degradant and minimization of degradation to phenytoin. If the pH is maintained at a lower or higher value, then the degradation pattern changes, with earlier than expected product failure.

6 Claims, No Drawings

STABLE PHARMACEUTICAL COMPOSITION OF 3-(HYDROXYMETHYL)-5,5-DIPHENYLHYDANTOIN DISODIUM PHOSPHATE ESTER

BACKGROUND OF THE INVENTION 5,5-Diphenylhydantoin, phenytoin, is a commonly used drug for the treatment and management of epilepsy and other types of convulsive states. While phenytoin is widely used for the treatment of these conditions, it has an extremely low solubility and, consequently, low bioavailability. Phenytoin is a high melting, weakly acidic drug exhibiting poor solubility in water. These properties lead to erratic absorption after oral dosing with both the free acid and the sodium salt. See the papers by S. A. Varia et al., Journal of Pharmaceutical Sciences 73(8): 1068-190, August 1984. For parenteral use, sodium phenytoin is formulated in an aqueous alkaline medium of pH 12 containing 40% propylene glycol and 10% ethanol. The parenteral dosage form can be painful if the intravenous injection is rapid and the free acid appears to precipitate at intramuscular injection sites. Emergency use of parenteral phenytoin, namely, in cases of controlling seizures in patients with head injuries, may require the administration of the drug intramuscularly. To be clinically acceptable, intramuscular administration of a drug should cause minimal tissue damage at the injection site. Intramuscular administration of sodium phenytoin has been reported to be painful, probably due to the precipitation of phenytoin. It has also been shown to cause hemorrhage, hematoma and necrosis at the injection site in cats and rabbits.

U.S. Pat. No. 4,260,769 issued Apr. 7, 1981, and the previously noted articles by S. A. Varia et al. in the Journal of Pharmaceutical Sciences, disclose various prodrugs of phenytoin with more desirable physico-chemical properties. In particular, patent 4,260,769 and the noted publications disclose the phenytoin prodrug 3-(hydroxymethyl)-5,5diphenylhydantoin disodium phosphate ester which is shown to have physicochemical properties that are suitable for a prodrug of phenytoin for parenteral use. S. A. Varia and V. J. Stella, at pages 1087-1090 in the Journal of Pharmaceutical Sciences, report that the compound did not exhibit any tissue damage after subcutaneous or intramuscular administration and thus, would be a suitable prodrug candidate for intramuscular delivery of phenytoin. However, this prodrug tends to degrade with the subsequent precipitation of phenytoin. Common methods used to delay the precipitation point involve modifying the formulation to contain agents that might solubilize larger quantities of the degradation product. These agents include alcohol, propylene glycol, L-arginine, sodium desoxycholate, polysorbate-80, and various combinations of these compounds.

SUMMARY OF THE INVENTION

It has been found that the prodrug, 3-(hydroxymethyl)-5,5-diphenylhydantoin disodium phosphate ester, is stable in an aqueous system when maintained at a pH of about 8.3 to 9.4 to produce diphenylglycinamide as the primary degradant with minimal quantities of phenytoin. A preferred pharmaceutical composition would contain 35 to 130 mg/mL of the prodrug and 0.05 to 0.2 M buffer.

DETAILED DESCRIPTION OF THE INVENTION

The stability of the prodrug has always been limited by the occurrence of precipitation in the product. This precipitation has been related to the degradation of prodrug to phenytoin and the subsequent precipitation of phenytoin.

A preferred pharmaceutical composition would contain:

prodrug: 35 to 180 mg/mL
alcohol: USP 0 to 25%
propylene glycol: 0 to 25%
L-arginine: 0 to 0.2 M
sodium desoxycholate: 0 to 0.1 M
polysorbate-80: 0 to 1.5%
tromethamine: 0.05 to 0.2 M
in water for injection with the pH adjusted from 8 to 10 with hydrochloric acid or sodium hydroxide.

The pH range found to provide the greatest stability is a pH of about 8.3 to 9.4. In this pH range, the choice of buffers is limited, namely, to buffers effective to maintain a pH of about 8 to 10. In addition to tromethamine, tris-(hydroxymethyl)aminomethane; other buffers which can be used are bicine, N-N-bis(2-hydroxyethyl)-2-aminoethanesulfonic acid; tricine, N-tris(hydroxymethyl)methylglycine; sodium bicarbonate; glycylglycine; Hepes, N-2-hydroxyethylpiperazine-N'-2-ethanesulfonic acid; Hepps, N-2-hydroxyethylpiperazine-N'3-propane-sulfonic acid; sodium phosphate; and Taps, 3{[tris(hydroxymethyllmethylamino}propanesulfonic acid. Tromethamine, bicine or tricine are preferred. Suitable wetting agents in addition to polysorbate-80 are: polyoxamer 188 and polyoxyethylene fatty acid esters. A more specific composition would be 75 mg/mL prodrug; 0.1 M tromethamine and a pH of about 8.3 to 9.

The following tables illustrate the stability of a composition of the phenytoin prodrug comprising 75.7 mg/mL prodrug, 0.1 M tromethamine, pH adjusted to 9.1 with HCl.

TABLE I

| | | | | | | PERCENT AS PRODRUG | | |
|---|---|---|---|---|---|---|---|---|
| | AGE | | | INITIAL | CURRENT | | | PERCENT |
| LOT | (MO) | TEMP | PH | POTENCY | POTENCY | DIZ | FORM | RECOVERY |
| 2131 | 27 | RT | 8.9 | 98.22 | 93.75 | 0.196 | 5.553 | 101.30 |
| 2140 | 27 | RT | 8.9 | 96.42 | 92.13 | 0.172 | 5.042 | 100.96 |
| 2183 | 24 | RT | 8.8 | 98.06 | 94.30 | 0.130 | 4.450 | 100.84 |
| 2183 | 24 | RT | 8.8 | 98.06 | 94.30 | 0.135 | 4.314 | 100.70 |
| 2211 | 23 | RT | 8.3 | 104.52 | 103.38 | 0.033 | 1.509 | 100.38 |
| 2224 | 23 | RT | 8.9 | 103.75 | 97.24 | 0.155 | 4.349 | 98.07 |
| 2293 | 16 | RT | 8.5 | 100.91 | 99.11 | 0.055 | 1.747 | 100.00 |
| 2295 | 16 | RT | 8.3 | 101.49 | 99.04 | 0.040 | 1.303 | 98.91 |
| 2327 | 9 | 40 | 8.9 | 100.42 | 93.74 | 0.382 | 7.893 | 101.59 |
| 2327 | 8 | 40 | 8.9 | 101.41 | 94.88 | 0.342 | 7.450 | 101.24 |
| 2358 | 7 | 40 | 8.9 | 98.70 | 94.34 | 0.251 | 6.653 | 102.58 |

MASS BALANCE OF FORMALDEHYDE IN DEGRADED PRODRUG

TABLE I-continued

| | | | | | MASS BALANCE OF FORMALDEHYDE IN DEGRADED PRODRUG | | |
|---|---|---|---|---|---|---|---|
| | AGE | | | INITIAL | CURRENT | PERCENT AS PRODRUG | | PERCENT |
| LOT | (MO) | TEMP | PH | POTENCY | POTENCY | DIZ | FORM | RECOVERY |
| 2360 | 7 | 40 | 8.9 | 99.63 | 94.61 | 0.246 | 5.364 | 100.59 |

DIZ = 5,5-DIPHENYL-4-IMIDAZOLIDINONE
FORM = FORMALDEHYDE

TABLE II

MASS BALANCE OF THE 75 MG/ML PHENYTOIN PRODRUG USING METHOD I

| LOT | AGE (MO) | TEMP | pH | INITIAL POTENCY | POTENCY | DEGRADATION PRODUCTS (PERCENT AS PRODRUG) | | | | | | PERCENT RECOVERY |
|---|---|---|---|---|---|---|---|---|---|---|---|---|
| | | | | | | PHEN | DPG | BZP | DIZ | UNKB | FORM | |
| 2131 | 27 | RT | 8.8 | 98.22 | 93.75 | 0.211 | 0.295 | 0.001 | 0.196 | 5.046 | 5.553 | 101.30 |
| 2140 | 27 | RT | 8.8 | 96.42 | 92.13 | 0.189 | 0.245 | 0.004 | 0.172 | 4.604 | 5.042 | 100.96 |
| 2183 | 24 | RT | 8.8 | 98.06 | 94.30 | 0.131 | 0.053 | 0.002 | 0.130 | 4.264 | 4.450 | 100.84 |
| 2183 | 24 | RT | 8.8 | 98.06 | 95.57 | 0.130 | 0.049 | 0.003 | 0.135 | 4.132 | 4.314 | 102.00 |
| 2211 | 23 | RT | 8.3 | 104.52 | 103.38 | 1.016 | 0.011 | 0.0003 | 0.033 | 0.482 | 1.509 | 100.38 |
| 2224 | 23 | RT | 8.9 | 103.75 | 97.24 | 0.106 | 0.047 | 0.0015 | 0.155 | 4.195 | 4.349 | 98.07 |
| 2293 | 16 | RT | 8.5 | 100.91 | 99.11 | 0.053 | 0.000 | 0.0005 | 0.055 | 1.694 | 1.747 | 100.00 |
| 2295 | 16 | RT | 8.3 | 101.49 | 99.04 | 0.059 | 0.000 | 0.0006 | 0.040 | 1.243 | 1.303 | 98.91 |
| 2327 | 9 | 40 | 8.8 | 100.42 | 93.74 | 1.485 | 1.147 | 0.013 | 0.382 | 5.248 | 7.893 | 101.59 |
| 2327 | 8 | 40 | 8.8 | 101.41 | 94.88 | 1.071 | 0.746 | 0.014 | 0.342 | 5.619 | 7.450 | 101.24 |
| 2358 | 7 | 40 | 8.8 | 98.70 | 94.34 | 0.769 | 0.404 | 0.006 | 0.251 | 5.474 | 6.653 | 102.58 |
| 2360 | 7 | 40 | 8.8 | 99.63 | 94.61 | 0.800 | 0.419 | 0.005 | 0.246 | 4.140 | 5.364 | 100.59 |
| | | | | | | | | | | AVERAGE RECOVERY | | 100.71 |

PHEN = PHENYTOIN
DPG = DIPHENYLGLYCINE
BZP = BENZOPHENONE
DIZ = 5,5-DIPHENYL-4-IMIDAZOLIDINONE
UNKB* = UNKNOWN B, CALCULATED AS FOLLOWS: UNKB = FORM - PHEN - DPG - BZP
FORM = FORMALDEHYDE
NOTE: Unknown B (UNKB) has been identified as diphenylglycinamide

TABLE III

NEW MASS BALANCE OF 75 MG/ML PRODRUG USING METHOD II

| LOT | AGE (MO) | TEMP | pH | 9653 PERCENT OF INITIAL | DEGRADATION PRODUCTS (PERCENT AS PRODRUG) | | | | PERCENT RECOVERY |
|---|---|---|---|---|---|---|---|---|---|
| | | | | | PHEN | DPG | DIZ | DPGA | |
| 2131 | 30 | RT | 8.8 | 93.06 | 0.141 | 0.243 | 0.174 | 5.144 | 98.76 |
| 2140 | 30 | RT | 8.8 | 94.79 | 0.148 | 0.247 | 0.182 | 5.240 | 100.61 |
| 2183 | 27 | RT | 8.8 | 98.40 | ND | 0.116 | 0.137 | 3.021 | 101.67 |
| 2211 | 25 | RT | 8.3 | 98.64 | 0.097 | 0.041 | 0.027 | 1.254 | 100.06 |
| 2224 | 24 | RT | 8.8 | 94.85 | 0.104 | 0.110 | 0.163 | 3.810 | 99.04 |
| 2293 | 18 | RT | 8.5 | 98.70 | ND | 0.080 | ND | 1.631 | 100.41 |
| 2295 | 18 | RT | 8.3 | 98.53 | ND | 0.032 | 0.034 | 1.163 | 99.76 |
| 2327 | 10 | 40 | 8.8 | 92.11 | 1.491 | 1.224 | 0.437 | 5.068 | 100.33 |
| 2358 | 9 | 40 | 8.8 | 93.21 | 1.110 | 0.757 | 0.329 | 4.153 | 99.56 |
| 2360 | 9 | 40 | 8.8 | 92.34 | 1.157 | 0.766 | 0.323 | 4.115 | 98.70 |
| | | | | | | | AVERAGE RECOVERY | | 99.89 |

PHEN = PHENYTOIN
DPG = DIPHENYLGLYCINE
DIZ = 5,5-DIPHENYL-4-IMIDAZOLIDINONE
DPGA = DIPHENYLGLYCINAMIDE (UNKB in Table II)
ND = NONE DETECTED Initially, it was proposed that phenytoin prodrug decomposed via a simple two-step pathway resulting in phenytoin. However, it has been determined that phenytoin is not the only decomposition product and could only account for a small portion of the degraded prodrug. The degradation pathway has been determined to proceed from phenytoin prodrug to formaldehyde, 5,5-diphenyl-4-imidazolidinone (DIZ), diphenylglycinamide, diphenylglycine, benzophenone, and phenytoin via the pathways described.

Overall Degradation Pathway(s)

The overall degradation pathway is shown in Scheme V. Many of the steps involved include consumption of hydroxyl, indicating that the pH of the formulated product should decrease with time. This has been observed in the routine stability program for this product. The addition of a buffer to prevent the pH from dropping significantly from its initial value over the lifetime of the product is required. Small changes in the degradation pathway occur as the pH drops. It is seen that as the pH drops the rate of phenytoin formation increases and the rate of DIZ formation decreases. This indicates that the proposed hydantoin ring opening by the phosphate appears to be the rate limiting step in the primary degradation pathway of phenytoin prodrug. However, formation of phenytoin increases and the solubility of phenytoin decreases as the pH is lowered thus, diminishing the shelf-life of the product due to the saturation of the aqueous solution and eventual precipitation of phenytoin. The chosen pH of the finished product allows the degradation to proceed such that the primary degradant is diphenylglycinamide, while minimal quantities of phenytoin are produced and shelf-life is maximized.

Mass Balance Determination

Several samples at room temperature and 40° C were analyzed to determine mass balance. Analysis of phenytoin prodrug potency, formaldehyde, 2,2-diphenylglycine, 5,5-diphenylhydantoin, 5,5-diphenyl-4-imidazolidinone and benzophenone concentrations were performed using the gradient HPLC method. Analysis of phenytoin prodrug potency, 2,2-diphenylglycine, 2,2-diphenylglycinamide (as 2,2-diphenylglycine). 5,5-diphenylhydantoin, and 5,5-diphenyl-4-imidazolidinone concentrations were determined using the isocratic HPLC method. Molar equivalents were calculated and mass balance results were determined and compared.

Method Statistics and Comparison

Method I—Gradient Method

Several standard curves of each compound were chromatographed for the determination of method linearity. The peak areas and heights were plotted versus respective concentrations to yield calibration curves. All standard curves typically had a correlation coefficient of >0.99. Standard peak heights or areas were shown to be within 4% of the linear regression line thereby passing pre-established system suitability requirements. Replicate injections of a standard solution of each compound were chromatographed. Relative standard deviations were less than 1.7% using peak areas and less than 2.2% using peak heights. These results confirm the method is precise.

The same dilutions of standards were used for determination of limit of detection and limit of quantitation. All standards were chromatographed. Peak areas were measured by the data system and linearity was confirmed. Data from standard curve injections before and after a set of sample injections were collected to determine the suitability and effectiveness of the HPLC system. Limits of quantitation were experimentally determined and are shown below.

|  | Peak Area | Peak Height |
|---|---|---|
| Diphenylglycine | 8.3 μg/mL | 27.7 μg/mL |
| Diphenylhydantoin | 0.5 μg/mL | 3.0 μg/mL |
| Diphenyl-4-imidazolidinone | 8.9 μg/mL | 1.5 μ/mL |
| Benzophenone | 0.05 μg/mL | 0.05 μg/mL |

Limits of detection were experimentally determined and are shown below.

|  | Peak Area or Height |
|---|---|
| Diphenylglycine | 1.0 μg/mL |
| Diphenylhydantoin | 0.3 μg/mL |
| Diphenyl-4-imidazolidinone | 0.5 μg/mL |
| Benzophenone | 0.01 μg/mL |

A combination standard curve containing 2,2-diphenylglycine, 5,5-diphenylhydantoin and 5,5-diphenyl-4-imidazolidinone was chromatographed several times for the determination of equality with individual standard curves. The peak areas and heights were plotted versus respective concentrations to yield calibration curves. Slopes and y-intercepts were compared to individual standards, confirming their equality. Replicate injections of a combination standard solution were chromatographed. Relative standard deviations were less than 1.7% using peak areas and less than 2.0% using peak heights with the exception of diphenylglycine, which was 3.09% using peak heights. This confirms the method is precise using the combination standard curve.

Mass Balance

Several samples kept at various lengths of time at room temperature and 40° C. were analyzed to determine mass balance. Initial and current potency, along with current formaldehyde concentration data, were used to determine mass balance. Diphenylglycine, diphenylhydantoin, diphenyl-4-imidazolidinone and benzophenone concentrations were chromatographically determined using Method I. From this data, mass balance was calculated. Initial and current potency values were converted to initial and current moles of phenytoin prodrug. Formaldehyde, diphenylglycine, diphenylhydantoin, diphenyl-4-imidazolidinone and benzophenone concentrations were converted to molar equivalents. Using the value of moles of formaldehyde, diphenylglycine, diphenylhydantoin and benzophenone, the moles of Unknown B (which later was determined to be diphenylglycinamide) were calculated using Equation 1.

$$\text{Unknown } B \text{ Moles*} = \text{Formaldehyde (moles)} - \text{diphenylglycine (moles)} - \text{diphenylhydantoin (moles)} - \text{benzophenone (moles)} \quad (1)$$

$$\text{Moles Determined} = \text{Current moles} + \text{Unknown } B \text{ (moles)*} + \text{diphenylglycine (moles)} + \text{diphenylhydantoin (moles)} + \text{diphenyl-4-imidazolidinone (moles)} + \text{benzophenone (moles)} \quad (2)$$

$$\frac{\% \text{ of Intitial}}{\text{Recovered}} = \frac{\text{Moles Determined}}{\text{Initial Moles}} \times 100 \quad (3)$$

*Unknown B was determined to be diphenylglycinamide

The percent recovery of 12 samples analyzed was 98.0 to 102.6% thereby proving mass balance (Table I).

Method II - Isocratic Method

Linearity

Standard curves were prepared and injected to determine the linearity of the isocratic method. In each case linear regression lines for diphenylglycine, 5,5-diphenyl-4-imidazolidinone and phenytoin had correlation coefficients of greater than 0.999. Diphenylglycinamide was identified as a compound of degradation, previously referred to as Unknown B. As no standard for diphenylglycinamide is available, the curve for diphenylglycine was used to determine the concentrations of the samples.

Precision of the isocratic method was performed only by analysis of several lots of degraded prodrug and comparing the results to the results of the gradient method (see Tables II and III). The results showed very favorable comparisons for all the degradants. The major difference is seen in the diphenylglycinamide (previously referred to as Unknown B) levels. As it was quantitated using diphenylglycine as a standard rather than by difference (Equation 1), a slight decrease was observed. These results indicate that quantitation by difference is only affected by the variation in the formaldehyde assay.

SCHEME V

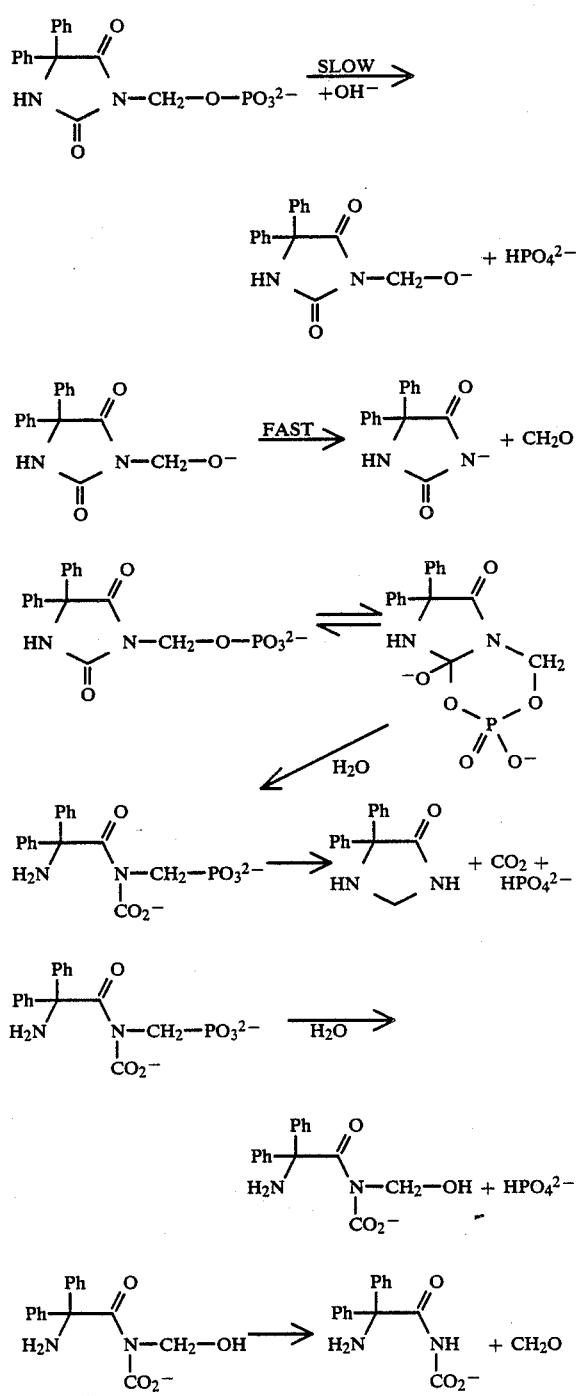

-continued
SCHEME V

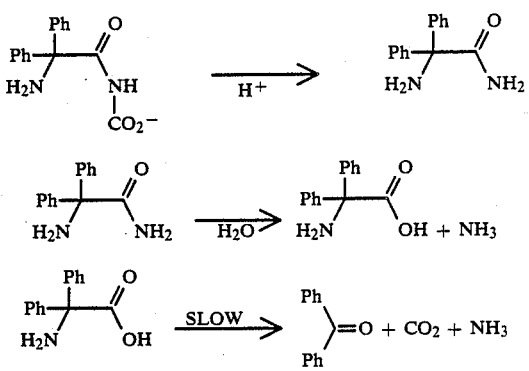

What is claimed is:

1. An injectable, aqueous pharmaceutical composition for the treatment of convulsive states comprising an effective amount of 3-(hydroxymethyl)-5,5-diphenylhydantoin disodium phosphate ester (phenytoin prodrug) for treating such convulsive states, said composition comprising about 35 mg to about 180 mg of prodrug/mL of solution and 0.05 to 0.2 M buffer; said composition having a pH range of about 8.3 to 9.4, the prodrug degrading in aqueous solution to produce diphenylglycinamide as the primary degradant with minimal quantities of phenytoin, the pH range of said composition acting to allow the degradation to proceed whereby the shelf-life of the prodrug in an aqueous composition is maximized.

2. The composition of claim 1 wherein the buffer is selected from the group comprising tromethamine, bicine and tricine.

3. The composition of claim 2 wherein the buffer is tromethamine.

4. The composition of claim 3 wherein the prodrug is present in the amount of 75 mg/mL.

5. The composition of claim 1 wherein the pH is about 8.3 to 9.

6. A method for the treatment of a convulsive state in a mammal comprising administering by subcutaneous or intramuscular administration to a mammal in need of such treatment an anti-convulsive amount of a stable, pharmaceutical composition of the prodrug 3-(hydroxymethyl)-5,5-diphenylhydantoin disodium phosphase ester, said composition comprising from about 35 to 130 mg/mL of prodrug, and from about 0.05 to 2 M of a buffer effective to maintain a pH of about 8.3 to 9.4 the prodrug degrading in aqueous solution to produce diphenylgylcinamide as the primary degradant with minimal quantities of phenytoin, the pH range of said composition acting to allow the degradiation to proceed whereby the shelf-life of the prodrug in an aqueous composition is maximized.

* * * * *